United States Patent [19]

Marschner et al.

[11] Patent Number: 5,290,482
[45] Date of Patent: Mar. 1, 1994

[54] SURFACTANT COMPOSITIONS COMPRISING BETAINE/COCOAMIDE COMPLEXES AND METHOD OF MAKING THE SAME

[75] Inventors: Frank W. Marschner, Whitehouse Station; Eugene E. Hardy, East Brunswick, both of N.J.

[73] Assignee: Colgate-Palmolive Company, New York, N.Y.

[21] Appl. No.: 891,519

[22] Filed: Jun. 1, 1992

[51] Int. Cl.$^5$ .................. C11D 1/90; C11D 1/94; C11D 3/32

[52] U.S. Cl. ................... 252/544; 252/546; 252/548; 252/DIG. 5; 252/DIG. 13

[58] Field of Search ......... 252/544, 546, 548, DIG. 5, 252/DIG. 13

[56] References Cited

U.S. PATENT DOCUMENTS

| | | | |
|---|---|---|---|
| 3,950,417 | 4/1976 | Verdicchio et al. | 252/545 |
| 3,964,500 | 6/1976 | Drakoff | 132/7 |
| 4,075,131 | 2/1978 | Sterling | 252/542 |
| 4,137,191 | 1/1979 | Lohr | 252/153 |
| 4,148,762 | 4/1979 | Koch et al. | 252/544 |
| 4,246,131 | 1/1981 | Lohr | 252/153 |
| 4,253,993 | 3/1981 | Ramsey, III et al. | 252/548 |
| 4,338,211 | 6/1982 | Stiros | 252/142 |
| 4,364,837 | 12/1982 | Pader | 252/173 |
| 4,435,300 | 3/1984 | Guth et al. | 252/117 |
| 4,443,362 | 4/1984 | Guth et al. | 252/545 |
| 4,490,355 | 12/1984 | Desai | 424/70 |
| 4,534,877 | 8/1985 | Russel et al. | 252/106 |
| 4,547,364 | 10/1985 | Brown | 424/70 |
| 4,636,329 | 1/1987 | Steuri | 252/106 |
| 4,704,226 | 11/1987 | Naylor | 252/162 |
| 4,704,272 | 11/1987 | Oh et al. | 424/70 |
| 4,741,855 | 5/1988 | Grote et al. | 252/173 |
| 4,938,953 | 7/1990 | Pena et al. | 424/70 |

*Primary Examiner*—Linda Skaling
*Assistant Examiner*—Erin Higgins
*Attorney, Agent, or Firm*—Robert C. Sullivan; Richard J. Ancel

[57] ABSTRACT

Betaine/cocoamide complexes are produced by providing an aqueous solution of a cocoamide selected from the group comprising coconut oil fatty amides and an alkaloid selected from the group consisting of betaines and emulsifying said aqueous solution to form the betaine/cocoamide complexes. Surfactant compositions are produced by combining the betaine/cocoamide complexes with a surfactant. The betaine/cocoamide complexes provide improved lather and conditioning properties and lower cloud/clear points to the compositions produced.

11 Claims, No Drawings

SURFACTANT COMPOSITIONS COMPRISING BETAINE/COCOAMIDE COMPLEXES AND METHOD OF MAKING THE SAME

FIELD OF INVENTION

This invention relates to novel betaine/cocoamide complexes and surfactant compositions comprising such complexes as well as methods of making the same. More particularly, it concerns a method for producing a conditioning agent comprising a betaine/cocoamide complex for use in surfactant compositions to provide improved lather and conditioning properties and lower cloud/clear points to the products produced.

BACKGROUND ART

Coconut oil fatty amides of the di or monoethanol types are widely known and used as viscosity builders, coemulsifiers and foam boosters in a variety of anionic surfactant products including shampoos and hand dishwashing liquids. Cocodiethanolamide is most widely used in shampoo compositions since it is a liquid at room temperature and requires no heat in formulations. See U.S. Pat. No. 4,534,877 to Russell et al.

Alternatively, cocomonoethanolamide is used in shampoo compositions to enhance foam. It's use is limited, however, since it is a solid, and requires melting and often special solubilizing techniques. It is commonly used in pre-emulsified form with ammonium or sodium xylene sulfonates. It can also be pre-emulsified in minor formula amounts of hot, anionic surfactant. U.S. Pat. No. 3,964,500 to Drakoff discloses the use of cocomonoethanolamide in shampoo formulations as a "suds" booster.

Cocoamidopropyl betaine is also a common shampoo ingredient used as a conditioning agent or foam booster to enhance the richness of the lather. See U.S. Pat. No. 4,490,355 to Desai. However, betaines are amphoteric compounds and when used in shampoo compositions form deposits on the hair follicles giving the appearance of greasy, unclean hair.

The prior art has disclosed shampoo compositions which contain cocoamides and betaines. U.S. Pat. No. 4,938,953 to Pena et al. discloses a conditioning shampoo comprising a fatty alcohol sulfate or fatty alcohol ether sulfate, cocamidopropyl betaine and cocoamide diethanolamine. As shown in Pena cocamidopropyl betaine and coconut oil derived amine oxides are typical examples of surfactant based conditioning agents. Thus it is shown that both betaine and certain cocoamides provide mild conditioning properties to the hair. These conditioning agents in addition to being substantive to the hair, frequently serve a dual role as a foam booster.

The present invention is directed to a method for producing novel betaine/cocoamide complexes. In particular, it concerns a method for producing a conditioning agent comprising a betaine/cocoamide complex for use in surfactant compositions. The betaine/cocoamide complexes provide conditioning properties and superior synergistic properties to compositions not offered by either the betaines or cocoamides alone. It will be appreciated that advantage over known compositions is obtained by providing such compositions which improve lather and conditioning characteristics as well as lower cloud/clear points for producing clear products.

Accordingly, it is a broad object of the invention to provide betaine/cocoamide complexes and methods of making the same.

A more specific object of the invention is to provide a conditioning agent comprising a betaine/cocoamide complex for use in surfactant compositions which improve lather and conditioning characteristics as well as lower cloud/clear points for producing clear products.

Another object of the invention is to provide surfactant compositions with improved lather and conditioning characteristics.

Another specific object of the invention is to provide a method for manufacture of surfactant compositions comprising a betaine/cocoamide complex and a surfactant to produce compositions with desired properties.

A further specific object of the invention is to provide a simplified process for producing surfactant compositions with improved lather and conditioning characteristics as well as lower cloud/clear points for clear products.

DISCLOSURE OF THE INVENTION

In the present invention, these purposes, as well as others which will be apparent, are achieved generally by providing betaine/cocoamide complexes for use in surfactant compositions. Such complexes provide compositions with improved lather and conditioning properties. In addition the complexes contribute to lower cloud/clear points to produce clear products and more level temperature/viscosity profiles.

The betaine/cocoamide complexes of the invention are produced by providing an aqueous solution of a cocoamide selected from the group comprising coconut oil fatty amides and an alkaloid selected from the group consisting of betaines, and emulsifying the solution to form the betaine/cocoamide complex.

The cocoamides used to form the complex have melting points at or above 90° F. Particular cocoamides used in the invention are selected from the group comprising cocomonoethanolamides which contain a chain length of C8 or greater, and preferably C14 or greater. Other cocoamides selected from the group comprising cocoisopropanolamides which contain a chain length of C12 or greater may also be used.

Betaines used in the invention contain a quaternium ammonium sulfonium or phosphonium cationic group and at least one carboxyl, sulfonate or sulfite anionic group. Specific betaines used to form the complex include carboxybetaine, sulfobetaine, sulfitobetaine, sulfabetaine, sulfoniobetaine or phosphoniobetaine.

The surfactant compositions of the invention are produced by combining the betaine/cocoamide complex with a surfactant. In preparing these compositions process and reaction conditions are controlled so that the cocoamide reacts with the betaine to form a betaine/cocoamide complex. It is critical to the invention process that this complex is formed prior to combining with the surfactant. If the cocoamide, betaine and surfactant are heated together and cooled, the complex does not form and desired physical and performance properties are not achieved.

The surfactants used in the invention include cationic, nonionic, amphoteric or anionic surfactants or mixtures thereof. Preferred surfactants include anionic surfactants selected from the group comprising fatty alcohol sulfates, fatty alcohol ether sulfates, alkyl benzene sulfonates, alkane sulfonates or olefin sulfonates.

In addition, sodium chloride and propylene glycol may be added to the compositions as viscosity controlling agents and formalin may be added as a preservative. Other additives comprising esters, silicones, fatty alcohols, lecithin, proteins, humectants, emollients and other compounds may also be added to the compositions to adjust the characteristics of the compositions.

Preferred applications of the method of the invention include use in the production of shampoo compositions, hair care compositions and other related products with conditioning properties. Advantageously, the method of the invention provides betaine/cocoamide complexes which impart conditioning properties and superior synergistic properties to compositions not offered by either betaines or cocoamides alone.

Other objects, features and advantages of the present invention will be apparent when the detailed description of the preferred embodiments of the invention are considered.

DETAILED DESCRIPTION OF THE PREFERRED EMBODIMENT

In accordance with the present invention betaine/cocoamide complexes for use in surfactant compositions are provided. Such complexes provide compositions with improved lather and conditioning properties. In addition the complexes contribute to lower cloud/clear points to produce clear products and more level temperature/viscosity profiles.

The betaine/cocoamide complexes of the invention are produced by providing an aqueous solution of a cocoamide selected from the group comprising coconut oil fatty amides and an alkaloid selected from the group consisting of betaines, and emulsifying the solution to form the betaine/cocoamide complex.

The cocoamides used to form the complex have melting points at or above 90° F. Particular cocoamides used in the invention are selected from the group comprising cocomonoethanolamides which contain a chain length of C8 or greater, and preferably C14 or greater. The cocomonoethanaloamides are present at a concentration in the range of 0.1 to 8% of the final composition. Other cocoamides selected from the group comprising cocoisopropanolamides which contain a chain length of C12 or greater may also be used.

Betaines used in the invention contain a quaternium ammonium sulfonium or phosphonium cationic group and at least one carboxyl, sulfonate or sulfite anionic group. Specific betaines used to form the complex include carboxybetaine, sulfobetaine, sulfitobetaine, sulfabetaine, sulfoniobetaine or phosphoniobetaine. The concentration of betaines used in the invention is in the range of 0.3 to 24% of the final composition. Cocamidopropyl betaine of various chain lengths is a preferred betaine used in the invention.

The surfactant compositions of the invention are produced by combining the betaine/cocoamide complex with a surfactant. In preparing these compositions process and reaction conditions are controlled so that the cocoamide reacts with the betaine to form a betaine/cocoamide complex prior to combining with the surfactant.

Specifically, an aqueous solution of a cocoamide selected from the group comprising coconut oil fatty amides and an alkaloid selected from a group comprising betaines is emulsified to form a betaine/cocoamide complex and then combined with a surfactant to produce the compositions of the invention.

The aqueous solution has a pH in the range of 7 to 11, dependent on the free amines present in the cocoamide used. The aqueous solution is emulsified by heating to temperatures at or above the melting point of the cocoamide, preferably in the range of 130° to 175° F. to form the betaine/cocoamide complex. The aqueous solution is then cooled below the melting point of the cocoamide, preferably below 90° F. to set the betaine/cocoamide complex. The betaine/cocoamide complex is then combined with a surfactant at preferred temperatures in the range of 60° to 100° F. to produce the compositions of the invention. The specific temperatures of each of the process steps vary depending on the melting point of the particular cocoamide used in the invention.

It is critical to the invention process that the betaine/cocoamide complex is formed prior to combining with the surfactant. If the cocoamide, betaine and surfactant are heated together and cooled, the complex does not form and desired physical and performance properties are not achieved.

The surfactants used in the invention include cationic, nonionic, amphoteric or anionic surfactants or mixtures thereof. Preferred surfactants include anionic surfactants selected from the group comprising fatty alcohol sulfates, fatty alcohol ether sulfates, alkyl benzene sulfonates, alkane sulfonates or olefin sulfonates. Specific anionic surfactants used in the invention include ammonium lauryl sulfate or sodium laureth sulfate. Generally, 0.5 to 13 wt. % of the betaine/cocoamide complex is combined with 5 to 25 wt. % of the anionic surfactant, preferably, 3 to 8% and 12 to 18% respectively, to produce the compositions of the invention.

In addition, sodium chloride and propylene glycol may be added to the compositions as viscosity controlling agents and formalin may be added as a preservative. Other additives comprising esters, silicones, fatty alcohols, lecithin, proteins, humectants, emollients and other compounds may also be added to the compositions to adjust the characteristics of the compositions.

The formation of betaine/cocoamide complexes provide conditioning properties and superior synergistic properties to compositions not offered by either betaines or cocoamides alone. The following formulas and test data illustrate the advantages of these complexes in surfactant systems, particularly with the anionic surfactant system comprised of ammonium lauryl sulfate.

Identification/Description of Amides

As shown in Table I below, five cocodiethanolamide's (CDEA) and five cocomonoethanolamide's (CMEA) with matched chain length distributions were examined. These materials were supplied by Mona Industries Inc., 76 East 24th Street, Paterson, N.J., 07544.

TABLE I

| Code Designation of Cocoamide Samples | | |
|---|---|---|
| CDEA | CMEA | Description |
| 705 | CMA | Processed from whole coconut oil with Glycerine as biproduct. |
| 1078 | CMA-MOD | Processed from whole cocofatty acids w/o Glycerine |
| 150LWA | LMA | Predominantly straight Lauryl C-12 |
| 150LM-WC | LM-MA | Lauryl 70% C12/Myristyl 30% C14 |
| GLT | CMA-S | Stripped C12–C18 100% Hydrogenated |

The following examples show what effect chain length distribution has on the properties of both CDEA and CMEA in two anionic surfactant systems, i.e. Sodium Laureth (2EO) Sulfate (SLES) and Ammonium Lauryl Sulfate (ALS)/Cocamidopropyl Betaine (CAPB) surfactant systems.

Shampoo compositions "A" and "B" were prepared and were tested for their effects on foam, cloud/clear points and viscosity/temperature profiles. The cocoamide samples used in each of the compositions are from Table I and were studied at levels of 0, 0.5, 1.0 and 2.0%.

Shampoo composition "A" was prepared by adding the cocoamide sample to an SLES/water mixture, in the amounts indicated below, applying heat to melt the cocoamide and then cooling the composition. Formalin and salt were then added.

| Shampoo "A" (Straight 10% SLES) | | | | |
|---|---|---|---|---|
| Water | 88.9 | 88.4 | 87.9 | 86.9 |
| Sodium Laureth (2EO) Sulfate | 10.0 | 10.0 | 10.0 | 10.0 |
| Cocoamide Sample | 0.0 | 0.5 | 1.0 | 2.0 |
| Formalin | 0.1 | 0.1 | 0.1 | 0.1 |
| Sodium Chloride | 1.0 | 1.0 | 1.0 | 1.0 |
| TOTAL | 100.0 | 100.0 | 100.0 | 100.0 |

Shampoo composition "B" was prepared by adding the cocoamide sample to betaine, in the amounts indicated below, and applying heat to emulsify the cocoamide followed by cooling to set the betaine/cocoamide complex. This mixture was then added to the ALS.

| Shampoo "B" (8% ALS/2% Betaine Blend) | | | | |
|---|---|---|---|---|
| Water | 89.5 | 89.0 | 88.5 | 87.5 |
| Ammonium Lauryl Sulfate | 8.0 | 8.0 | 8.0 | 8.0 |
| Cocoamide Sample | 0.0 | 0.5 | 1.0 | 2.0 |
| Cocamidopropyl Betaine | 2.0 | 2.0 | 2.0 | 2.0 |
| Sodium Chloride | 0.5 | 0.5 | 0.5 | 0.5 |
| TOTAL | 100.0 | 100.0 | 100.0 | 100.0 |

Foaming Properties of Shampoo Compositions "A" and "B"

Foaming properties of shampoo compositions "A" and "B" were studied with amide levels of 0, 0.5, 1.0 and 2.0%.

Laboratory Foam Tests were performed by inverting a 500 ml stoppered graduated cylinder 180° and returning it upright using an electric motor powered apparatus specifically designed for this purpose. Two determinations were taken; 8 cycles for flash foam and 12 additional cycles (total 20) for maximum foam properties. Flash foam tests determines the ease and speed of a shampoo to generate foam. Foam measurements after 20 cycles indicates the full lathering potential of a shampoo.

The following test solution was made and heated to 105°–108° F. with mixing to melt and dissolve the synthetic sebum used as soil.

| | gms |
|---|---|
| Shampoo | 15 |

| | gms |
|---|---|
| 150 ppm Hard Water | 85 |
| Synthetic Sebum | 3 |
| | 103 g |

Foam height was measured in ml along with drainage time in seconds after 20 cycles. The latter is the time required for most of the water (100 ml) to drain out of the foam, and high values denote better foam stability often associated with foam creaminess. Generally, more foam is best, however, a stable, wetter foam can also be equally desirable. Foam feel and slip on the hair and between the fingers is often a critical judgement of foam quality.

Cold water foam tests were also conducted using the aforementioned test procedure except 2 gms. oleic acid was used with a water temperature of 77° F. (25° C.). Cold Water foam performance is important for countries where cistern, lake or river water is used for shampooing.

| | gms |
|---|---|
| Shampoo | 15 |
| 150 ppm Hard Water | 85 |
| Oleic Acid | 2 |
| | 102 g |

CDEA Foam Test Results

CDEA Foam Properties were determined in hot and cold water using sebum and oleic acid soils respectively. All measurements listed below are in ml's.

(a) Hot Water with Sebum Soil

| Shampoo "A" (10 SLES + CDEA) | | | | |
|---|---|---|---|---|
| | % CDEA | | | |
| Chain Length | 0 | 0.5 | 1.0 | 2.0 |
| C12 | 320/18 | 345/21 | 355/24 | 360/24 |
| C8–C18 w/Glycerine | 320/18 | 315/54 | 325/25 | 345/21 |
| C8–C18 w/o Glycerine | 320/18 | 330/23 | 350/28 | 380/31 |
| 70C12/30C14 | 320/18 | 340/27 | 350/24 | 380/22 |
| C12–C18 Hydrogenated | 320/18 | 340/28 | 350/24 | 350/24 |

| Shampoo "B" (8 ALS/2 Betaine + CDEA) | | | | |
|---|---|---|---|---|
| | % CDEA | | | |
| Chain Length | 0 | 0.5 | 1.0 | 2.0 |
| C12 | 320/25 | 350/29 | 360/31 | 370/49 |
| C8–C18 w/Glycerine | 320/25 | 345/31 | 360/30 | 370/26 |
| C8–C18 w/o Glycerine | 320/25 | 340/17 | 355/27 | 370/31 |
| 70C12/30C14 | 320/25 | 330/29 | 350/34 | 390/34 |
| C12–C18 Hydrogenated | 320/25 | 375/29 | 375/34 | 395/38 |

(b) Cold Water with Oleic Acid Soil

| Shampoo "A" (10 SLES + CDEA) | | | | |
|---|---|---|---|---|
| | % CDEA | | | |
| Chain Length | 0 | 0.5 | 1.0 | 2.0 |
| C12 | 315/39 | 300/27 | 320/32 | 350/61 |
| C8–C18 w/Glycerine | 315/39 | 325/27 | 335/33 | 345/80 |

-continued

| Shampoo "A" (10 SLES + CDEA) | | | | |
|---|---|---|---|---|
| | % CDEA | | | |
| Chain Length | 0 | 0.5 | 1.0 | 2.0 |
| C8-C18 w/o Glycerine | 315/39 | 340/27 | 345/34 | 365/63 |
| 70C12/30C14 | 315/39 | 350/33 | 360/41 | 365/55 |
| C12-C18 Hydrogenated | 315/39 | 320/24 | 325/41 | 335/50 |

| Shampoo "B" (8 ALS/2 Betaine + CDEA) | | | | |
|---|---|---|---|---|
| | % CDEA | | | |
| Chain Length | 0 | 0.5 | 1.0 | 2.0 |
| C12 | 365/150 | 380/171 | 390/190 | 360/36 |
| C8-C18 w/Glycerine | 365/150 | 365/172 | 385/180 | 410/198 |
| C8-C18 w/o Glycerine | 365/150 | 310/31 | 340/88 | 350/160 |
| 70C12/30C14 | 365/150 | 365/193 | 420/191 | 450/245 |
| C12-C18 Hydrogenated | 365/150 | 390/210 | 410/195 | 420/185 |

CMEA Foam Test Results

CMEA Foam effectiveness was also determined in hot and cold water using Sebum and Oleic acid soils respectively. All measurements listed below are in ml's.

(a) Hot Water with Sebum Soil

| Shampoo "A" (10 SLES + CMEA) | | | | |
|---|---|---|---|---|
| | % CMEA | | | |
| Chain Length | 0 | 0.5 | 1.0 | 2.0 |
| C12 | 320/18 | 350/19 | 355/23 | 350/23 |
| C8-C18 w/Glycerine | 320/18 | 330/24 | 350/20 | 365/23 |
| C8-C18 w/o Glycerine | 320/18 | 320/26 | 335/24 | 370/20 |
| 70C12/30C14 | 320/18 | 315/17 | 360/21 | 385/38 |
| C12-C18 Hydrogenated | 320/18 | 350/18 | 375/21 | 385/22 |

| Shampoo "B" ( ALS/2 Betaine + CMEA) | | | | |
|---|---|---|---|---|
| | % CMEA | | | |
| Chain Length | 0 | 0.5 | 1.0 | 2.0 |
| C12 | 320/25 | 350/24 | 345/22 | 345/20 |
| C8-C18 w/Glycerine | 320/25 | 310/23 | 335/28 | 355/29 |
| C8-C18 w/o Glycerine | 320/25 | 320/21 | 360/34 | 385/37 |
| 70C12/30C14 | 320/25 | 310/19 | 350/27 | 375/26 |
| C12-C18 Hydrogenated | 320/25 | 350/21 | 365/27 | 375/26 |

(b) Cold Water with Oleic Acid Soil

| Shampoo "A" (10 SLES + CMEA) | | | | |
|---|---|---|---|---|
| | % CMEA | | | |
| Chain Length | 0 | 0.5 | 1.0 | 2.0 |
| C12 | 315/39 | 275/28 | 300/54 | 310/64 |
| C8-C18 w/Glycerine | 315/39 | 320/42 | 325/30 | 335/23 |
| C8-C18 w/o Glycerine | 315/39 | 350/56 | 350/34 | 365/31 |
| 70C12/30C14 | 315/39 | 320/27 | 335/39 | 350/65 |
| C12-C18 Hydrogenated | 315/39 | 320/26 | 330/37 | 340/39 |

| Shampoo "B" (8 ALS/2 Betaine + CMEA) | | | | |
|---|---|---|---|---|
| | % CMEA | | | |
| Chain Length | 0 | 0.5 | 1.0 | 2.0 |
| C12 | 365/150 | 395/229 | 355/189 | 345/180 |
| C8-C18 w/Glycerine | 365/150 | 405/390 | 415/420 | 440/501 |
| C8-C18 w/o Glycerine | 365/150 | 410/182 | 420/225 | 455/331 |
| 70C12/30C14 | 365/150 | 420/237 | 425/354 | 430/386 |
| C12-C18 Hydrogenated | 365/150 | 370/151 | 420/202 | 440/290 |

The results shown above indicate that foam increases with increased cocoamide levels. Preferred chain lengths for the SLES/CDEA systems are C8 to C18 without glycerine and C12 to C14, 70/30 ratios. Higher chain lengths such as C12 to C14 70/30 ratios and C12 to C18 hydrogenated are preferred for ALS/Betaine/CDEA systems. The hot water foam tests showed that these higher chain lengths are also preferred for CMEA with SLES or ALS/Betaine systems. Whereas the cold water foam tests results indicate performance is better with the CMEA having a lower C8 to C18 without glycerine chain length.

Effect of Cocomides on Cloud/Clear Points

The cloud point is the temperature at which the shampoo begins to cloud as it is chilled. The clear point is the temperature at which the shampoo clears completely as the temperature is raised from the frozen state. Cloud/clear points below 50° F. are desirable for clear shampoos. A simple apparatus consisting of a test tube, thermometer, and a metal ring stirrer is used to determine the cloud/clear (C/C) points of compositions "A" and "B".

Straight SLES and ALS have C/C points of about 29/45 (F) and 37/53 (F) respectively. The C/C points of Shampoos A and B with 2% cocoamide are reported below.

| | C/C Points (°F.) with CDEA | |
|---|---|---|
| Shampoo | "A" 10 SLES/2 CDEA | "B" (8 ALS/2 Betaine/2 CDEA) |
| C12 | 20/31 | 39/43 |
| C8-C18 w/Glycerine | 29/38 | 32/46 |
| C8-C18 w/o Glycerine | 29/40 | 34/45 |
| 70 C12/30 C14 | 21/36 | 32/42 |
| C12-C18 Hydrogenated | 27/41 | 32/44 |

| | C/C Points (°F.) With CMEA | |
|---|---|---|
| Shampoo | "A" 10 SLES/2 CMEA | "B" (8 ALS/2 Betaine/2 CMEA) |
| C12 | 37/64 | 61/36/31/47* |
| C8-C18 w/Glycerine | 31/58 | 55/33/31/47* |
| C8-C18 w/o Glycerine | 31/56 | 55/33/25/42* |
| 70 C12/30 C14 | 40/64 | 32/43 |
| C12-C18 Hydrogenated | 35/60 | 31/44 |

*Cloudy/Clear/Cloudy/Clear Double phases

As noted above, C/C points were relatively low for all CDEA formulations in either surfactant base. C/C points were very high for all CMEA Shampoo composition A formulations. Shampoo composition B with the three CMEA's of lowest average chain length gave two abnormal cloud/clear phases. The two higher molecular weight cocoamides had normal but unexpectedly low cloud/clear points indicating the formation of a Betaine/CMEA complex.

Study of Betaine/CMEA Complexes with Shampoo Composition "B"

The following temperature controlled methods were used to study conditions required for the formation of a Betaine/CMEA complex.

Control Method #1—CMEA was added to hot ALS, the mixture was stirred and cooled, then Betaine and water were added.

Complex Method #2—CMEA was added to hot Betaine solution, the mixture was stirred and cooled. The cold mixture was added to an ALS/water mixture at room temperature.

C/C Points of Shampoo Composition B—Complex Methods 1 and 2

The C/C points of Shampoo composition B, prepared using complex methods 1 and 2 are reported below.

|  | Control Method 1 (°F.) | Complex Method 2 (°F.) |
| --- | --- | --- |
| C12 | 62/34/30/39 | 58/34/21/34 |
| C8-C18 w/Glycerine | 48/34/31/36 | 30/38 Heat to 120 F/Cool = 31/36 |
| C8-C18 w/o Glycerine | 54/36/30/33 | 31/36 |
| 70C12/30 C14 | 60/39/33/39 | 33/37 |
| C12-C18 Hydrogenated | 60/37/31/36 | 34/36 |

All shampoo compositions using Method 1 gave high cloud/clear points and went through two cloud/clear phases. All shampoos using Method 2, except (C12) Lauramide MEA, provided desirable low cloud/clear points indicating the formulation of the Betaine/CMEA Complex.

The shampoo with C8-C18 CMEA w/Glycerine was reheated to 120° F./cooled, then C/C points rechecked. The same values were obtained indicating the complex is stable up to 120° F. (our maximum aging temperature).

Foam Properties of Shampoo Composition B—Complex Methods 1 and 2

Foam properties were determined after 8 (Flash) and 20 cycles (final foam reading).

Foam Tests—Shampoo Composition B

| Foam Tests - Shampoo Composition B (8 ALS / 2 Betaine / 2 CMEA) Height (ml) / Drainage Time (sec) | | | | |
| --- | --- | --- | --- | --- |
|  | Control Method 1 (°F.) | | Complex Method 2 (°F.) | |
|  | Flash 8 Cycles | Final 20 Cycles | Flash 8 Cycles | Final 20 Cycles |
| C12 | 245 | 325/17 | 255 | 330/23 |
| C8-C18 w/Glycerine | 240 | 325/21 | 275 | 365/30 |
| C8-C18 w/o Glycerine | 235 | 300/18 | 270 | 380/30 |
| 70 C12/30 C14 | 235 | 285/14 | 240 | 320/24 |
| C12-C18 Hydrogenated | 215 | 275/17 | 260 | 315/24 |

Samples which formed the betaine/CMEA complex with Method 2 out-foamed all others. Since Lauramide MEA did not form the complex, comparable foam properties were observed with both methods.

Temperature/Viscosity Profiles—Shampoo Composition B—Complex Methods 1 and 2

Shampoo compositions B containing 2% CMEA were examined for viscosity over a wide temperature range of 35°–120° F. The results are shown in Table II below.

TABLE II

| Temperature/Viscosity Profile Shampoo Composition B (ALS/Betaine) | | | | | | | |
| --- | --- | --- | --- | --- | --- | --- | --- |
| | Control Method 1 (Complex Method 2) Temp. °F. | | | | | | |
| CMEA | 35 | 45 | 55 | 65 | 77 | 100 | 120 |
| C12 | 4,520 | 34,080 | 65,600 | 67,480 | 28,680 | 6,970 | 1,330 |
|  | (4,800) | (39,000) | (55,000) | (30,000) | (16,000) | (7,000) | (2,000) |
| C8-C38 | 1,900 | 12,160 | 16,850 | 21,000 | 19,120 | 2,680 | 380 |
| w/Glycerine | (440) | (820) | (2,050) | (3,350) | (3,950) | (440) | (220) |
| C8-C18 | 1,120 | 6,520 | 13,860 | 19,080 | 17,400 | 5,280 | 720 |
| w/o Glycerine | (480) | (200) | (4,650) | (6,360) | (12,000) | (1,680) | (310) |
| 70 C12/30 C14 | 2,040 | 39,160 | 60,800 | 34,020 | 19,640 | 5,450 | 800 |
|  | (1,530) | (9,000) | (16,290) | (18,300) | (17,000) | (6,600) | (1,900) |
| C12-C18 Hydrogenated | 1,060 | 6,680 | 13,020 | 15,120 | 16,160 | 1,220 | 320 |
|  | (1,380) | (5,505) | (16,050) | (41,000) | (15,000) | (6,500) | (1,340) |

The betaine/CMEA complex was also found to alter viscosity properties of a shampoo formulation. Lauramide MEA gave relatively comparable viscosities using both methods but other CMEA's which were shown to form the Betaine/CMEA complex differed significantly in viscosity as illustrated in Table II.

Shampoo Composition Study

The following study illustrates the application of other betaine/cocoamide complexes with surfactant systems, particularly SLES systems used in the formulation of shampoo compositions.

A study was taken to compare the sensory signals of the shampoo compositions as disclosed in Examples I and II below. Example I shampoo composition was used as a control and only contained the cocoamide CDEA, therefore no betaine/cocoamide complex was included in the formulation. Example II shampoo composition contained a betaine/cocoamide complex comprised of CMEA and Laurimidopropyl betaine.

EXAMPLE I

| CHEMICAL NAME | CONCEN. (%) |
| --- | --- |
| Softened Water - Irradiated | 72.9500000 |
| 70/% C12-14 Alcohol EO 2:1 NA Sulfate | 13.5000000 |
| 25% Salt Solution | 6.0000000 |
| Cocodiethanolamide | 3.0000000 |
| Dehycont PK771/Euperlan PK771 (Henkel) | 3.0000000 |
| D&C Yellow No. 10/CI 47005 - 0.01% Solution | 0.6700000 |
| Amouage 9867 Shampoo Perfume | 0.4000000 |
| Citric Acid - 50% Solution | 0.2170000 |
| EDTA - Mixed Sodium Salt | 0.1300000 |
| FD&C Blue No. 1-0.1% Solution | 0.0830000 |
| Quaternium 15 | 0.0500000 |
| TOTAL = | 100.0000000 |

EXAMPLE II

| CHEMICAL NAME | CONCEN. (%) |
| --- | --- |
| Softened Water - Irradiated | 77.9500000 |
| 70/% C12-14 Alcohol EO 2:1 NA Sulfate | 12.0000000 |
| Dehycont PK771/Euperlan PK771 (Henkel) | 3.0000000 |
| Laurimidopropyl Betaine | 2.0000000 |
| Sodium N Decyl Sulfate | 1.5000000 |
| Cocomonoethanolamide (C12-C18 Hydrogenated) | 1.0000000 |
| Table Salt | 1.0000000 |
| D&C Yellow No. 10/CI 47005 - 0.01% Solution | 0.6700000 |
| Amouage 9867 Shampoo Perfume | 0.4000000 |
| Citric Acid - 50% Solution | 0.2170000 |
| EDTA - Mixed Sodium Salt | 0.1300000 |
| FD&C Blue No. 1-0.1% Solution | 0.0830000 |
| Quaternium 15 | 0.0500000 |
| TOTAL = | 100.0000000 |

The shampoo in Example I was prepared by dissolving EDTA salt and SLES in water. In a separate vessel, perfume was dissolved in CDEA and the mixture was added to the SLES solution. Color and quaternium 15 preservative and dehycont PK771 pearlizer concentrate were comixed in order. Citric acid solution was then added to adjust the pH of the composition to 7.0 to 7.5. Viscosity was adjusted by the addition of salt.

The shampoo in Example II was prepared by dissolving EDTA salt and SLES in water. In a separate vessel betaine and CMEA were heated to about 165° C. with mixing to form a betaine/CMEA complex. The solution was then cooled to about 80° C. to set the emulsion complex. This complex was then added to the SLES solution. Sodium N Decyl Sulfate was then added followed by perfume, colors, and Quaternium 15 preservative. Citric acid solution was added to adjust the pH to 7.0 to 7.9. Viscosity of the composition was adjusted by the addition of salt.

Methodology

This half-head shampoo study was implemented as a double-blind, within subject design, single session application counterbalanced for comparison of shampoo compositions of Example I and II. The study used twenty participants all of whom were female, minimum age 18, with normal to oily hair. Monadic evaluations were performed by a trained, licensed cosmetologist. Examples I and II were evaluated on foam attributes after first and second applications, wet hair attributes, and dry hair attributes.

Brief Conclusions:

Results of this study showed that Example II shampoo composition foam had significantly more foam volume than Example I shampoo composition foam (2nd application). Example II shampoo composition also left the hair significantly cleaner, drier, softer, easier to comb (i.e. ease of snap removal) and significantly less coated and less oily than Example I shampoo composition for both the wet and dry hair attributes. Moreover, the Example II shampoo composition also left the hair significantly easier to comb while wet (i.e. ease of comb slip) but with significantly more static while dry than the Example I formula.

The following data reflects the means for the significant differences for the wet and dry attributes in Examples I and II. The 1 to 7 Unipolar Rating Scale was: 1=not at all and 7=extreme.

|  | Example I | Example II |
| --- | --- | --- |
| Foam Attribute |  |  |
| Foam Volume | 6.75 | 7.00 |
| Wet Attributes |  |  |
| Clean Feel | 6.10 | 6.60 |
| Coated Feel | 2.65 | 2.00 |
| Soft Feel | 5.45 | 6.10 |
| Oily Feel | 2.85 | 2.00 |
| Dry Feel | 2.15 | 3.00 |
| Ease of Snag Removal | 5.30 | 5.90 |
| Ease of Comb Slip | 5.45 | 5.85 |
| Dry Attributes |  |  |
| Clean Feel | 6.00 | 6.30 |
| Coated Feel | 2.70 | 2.05 |
| Soft Feel | 5.95 | 6.60 |
| Oily Feel | 2.85 | 2.00 |
| Dry Feel | 2.15 | 2.95 |
| Ease of Snag Removal | 5.65 | 5.95 |
| Static | 3.55 | 4.10 |

It will be recognized by those skilled in the art that the betaine/cocoamide complexes of the invention have wide applications including use in the production of shampoo compositions, hair care products and other related products with conditioning properties. Advantageously, the method of the invention provides betaine/cocoamide complexes which impart conditioning properties and superior synergistic properties to compositions not offered by either betaines or cocoamides alone.

Numerous modifications are possible in light of the above disclosure incorporating the use of other cocoamides, betaines or cationic, nonionic, amphoteric or anionic surfactant systems.

Therefore, although the invention has been described with respect to illustrations and examples thereof it is not to be limited to those because it is considered that one of skill in the art will be able to utilize substitutes and equivalents to make such compositions without departing from the scope and spirit of the invention as defined in the claims appended hereto.

We claim:

1. A conditioning agent comprising a betaine/cocoamide complex formed from an emulsification of a betaine and a cocoamide, having a melting point at or about 90° C., selected from the group consisting of cocomonoethanolamides which contain chain length distributions of C8 to C18 or cocoisopropanolamides which contain chain length distributions of C12 to C18; wherein an emulsion is formed by heating to temperatures at or above the melting point of said cocoamide and said emulsion is then cooled below the melting point of said cocoamide to set the betaine/cocoamide complex.

2. The conditioning agent according to claim 1, wherein said betaine is a carboxybetaine, sulfobetaine, sulfitobetaine, sulfabetaine, sulfoniobetaine or phosphoniobetaine.

3. The conditioning agent according to claim 1, wherein said betaine contains a quaternium ammonium sulfonium or phosphonium cationic group and at least one carboxyl, sulfonate or sulfite anionic group.

4. The conditioning agent according to claim 1, wherein 0.5 to 13 wt. % of said betaine/cocoamide complex is combined with 5 to 25 wt. % of a cationic, nonionic, amphoteric or anionic surfactant or mixtures thereof.

5. The conditioning agent according to claim 1, wherein said betaine/cocoamide complex is combined with an additional surfactant to produce shampoo compositions, hair care products and other related products with conditioning properties.

6. A surfactant composition comprising 0.5 to 13 wt. % of a betaine/cocoamide complex and 5 to 25 wt. % of an additional surfactant, wherein said betaine/cocoamide complex is formed from an emulsification of a betaine and a cocoamide, having a melting point at or above 90° F., selected from the group consisting of cocomonoethanolamides which contain length distributions of C8 to C18 or cocoisopropanolamides which contain chain length distributions of C12 to C18; in which an emulsion is formed by heating to temperatures at or above the melting point of said cocoamide and said emulsion is then cooled below the melting point of said cocoamide to set the betaine/cocoamide complex, said betaine/cocoamide complex is then combined with said additional surfactant.

7. The surfactant composition according to claim 6, wherein said betaine is a carboxybetaine, sulfobetaine, sulfitobetaine, sulfabetaine, sulfoniobetaine or phosphoniobetaine.

8. The surfactant composition according to claim 6, wherein said additional surfactant is a cationic, nonionic, amphoteric or anionic surfactant or mixtures thereof.

9. The surfactant composition according to claim 6, wherein said additional surfactant is an anionic surfactant selected from the group consisting of fatty alcohol sulfates, fatty alcohol ether sulfates, alkyl benzene sulfonates, alkane sulfonates or olefin sulfonates.

10. The surfactant composition according to claim 6, further comprising additives selected from the group consisting of esters, silicones, fatty alcohols, lecithin, proteins, humectants, and emollients.

11. The surfactant composition according to claim 6 wherein the concentration of said cocoamide is 0.1 to 8.0% of the surfactant compositions and the concentration of said betaine is 0.3 to 24% of the surfactant composition.

* * * * *

UNITED STATES PATENT AND TRADEMARK OFFICE
CERTIFICATE OF CORRECTION

PATENT NO.  : 5,290,482

DATED       : March 1, 1994

INVENTOR(S) : Frank W. Marschner and Eugene E. Hardy

It is certified that error appears in the above-identified patent and that said Letters Patent is hereby corrected as shown below:

Col. 11, line 49, after 165° delete "C" and insert -- F --;

Col. 11, line 51, after 80° delete "C" and insert -- F --; and

Claim 1, Col. 12, line 65 after 90° delete "C" and insert -- F --.

Signed and Sealed this

Twenty-first Day of March, 1995

Attest:

BRUCE LEHMAN

Attesting Officer     Commissioner of Patents and Trademarks